United States Patent
Malinowski

(10) Patent No.: US 8,998,986 B1
(45) Date of Patent: Apr. 7, 2015

(54) NASAL STENT

(71) Applicant: Zdzislaw B. Malinowski, Castaic, CA (US)

(72) Inventor: Zdzislaw B. Malinowski, Castaic, CA (US)

( * ) Notice: Subject to any disclaimer, the term of this patent is extended or adjusted under 35 U.S.C. 154(b) by 3 days.

(21) Appl. No.: 13/936,023

(22) Filed: Jul. 5, 2013

(51) Int. Cl.
 *A61F 2/18* (2006.01)
 *A61F 2/86* (2013.01)

(52) U.S. Cl.
 CPC ... *A61F 2/18* (2013.01); *A61F 2/86* (2013.01); *A61F 2/186* (2013.01)

(58) Field of Classification Search
 USPC .......................................................... 623/10
 See application file for complete search history.

(56) References Cited

U.S. PATENT DOCUMENTS

| | | |
|---|---|---|
| 513,458 A | 1/1894 | Dayton |
| 851,048 A | 4/1907 | Woodward |
| 1,014,076 A | 1/1912 | McConnell |
| 1,069,459 A | 8/1913 | Myles |
| 1,077,574 A | 11/1913 | Woodward |
| 1,135,675 A | 4/1915 | Dixon |
| 1,255,578 A | 2/1918 | Boxley |
| 1,256,188 A | 2/1918 | Wilson |
| 1,481,581 A | 10/1922 | Woodward |
| 1,597,331 A | 7/1925 | Thurston et al. |
| 1,672,591 A | 8/1927 | Wells |
| 1,709,740 A | 9/1927 | Gogers |
| 1,743,993 A | 11/1928 | Washington |
| 1,839,606 A | 2/1930 | Simmons |
| 2,010,485 A | 2/1930 | Heath |
| 2,335,936 A | 9/1940 | Hanlon |
| 2,515,756 A | 8/1947 | Bove |
| 2,569,743 A | 4/1949 | Carlock |
| 3,710,799 A | 1/1973 | Caballero |
| 4,414,977 A | 11/1983 | Razakhany |
| 4,759,365 A | 7/1988 | Askinazy |
| 5,601,594 A | 2/1997 | Best |
| 5,618,299 A | 4/1997 | Khosravi et al. |
| 5,665,104 A | 9/1997 | Lee |
| 5,895,409 A | 4/1999 | Mehdizadeh |
| 5,931,852 A | 8/1999 | Brennan |
| 6,004,342 A | 12/1999 | Filis |
| 6,238,411 B1 | 5/2001 | Thorner |
| 6,270,512 B1 | 8/2001 | Rittmann |
| 6,386,197 B1 | 5/2002 | Miller |
| 6,562,057 B2 | 5/2003 | Santinh |
| 6,569,191 B1 | 5/2003 | Hogan |
| 6,626,172 B1 | 9/2003 | Karow et al. |
| 6,863,066 B2 | 3/2005 | Ogle |

(Continued)

FOREIGN PATENT DOCUMENTS

| | | |
|---|---|---|
| EP | 0754016 | 9/2003 |
| WO | WO2007065408 | 6/2007 |

OTHER PUBLICATIONS alaxo.com, The AlaxoLito Nasal Stent, Alaxo Gmbh 2008-2013 / MO, May 6, 2013.

*Primary Examiner* — Suzette J Gherbi

(57) ABSTRACT

A nasal valve retention stent assembly is positionable within a person's nasal cavity to enlarge the nasal cavity and promote easier breathing through the person's nose. The assembly includes a frame having a pair of ends and a plurality of rib elements extending between and being attached to each of the ends. The rib elements are arched between the ends to form a cage like structure having a hollow interior. The rib elements are spaced from each other such that air freely flows through the frame. The frame is positionable within an inner nasal valve of the nose.

16 Claims, 12 Drawing Sheets

(56) References Cited

U.S. PATENT DOCUMENTS

| | | |
|---|---|---|
| 6,978,781 B1 | 12/2005 | Jardan |
| 7,055,523 B1 | 6/2006 | Brown |
| 7,105,008 B2 | 9/2006 | Maryanka |
| 7,347,209 B2 | 3/2008 | Bovo |
| 7,390,331 B2 | 6/2008 | Santin et al. |
| 7,563,271 B2 | 7/2009 | Howard |
| 7,727,252 B2 | 6/2010 | Maryanka |
| 7,740,643 B2 | 6/2010 | Maryanka |
| 7,846,198 B2 * | 12/2010 | Hogendijk .................. 623/1.22 |
| 7,862,608 B2 * | 1/2011 | Hogendijk et al. .......... 623/1.22 |
| 7,905,899 B2 | 3/2011 | Funabashi |
| 7,997,266 B2 | 8/2011 | Frazier et al. |
| 8,048,102 B2 | 11/2011 | Thomas |
| 8,182,504 B2 | 5/2012 | Yazdi |
| 8,235,051 B2 | 8/2012 | Soderberg |
| 8,241,316 B2 | 8/2012 | Oberle |
| 8,246,647 B2 | 8/2012 | Wien |
| 8,262,688 B2 | 9/2012 | Santin |
| 8,277,477 B2 | 10/2012 | Oberle |
| 8,361,141 B2 | 1/2013 | Hansen |
| 2002/0169501 A1 | 11/2002 | Penn et al. |
| 2004/0147954 A1 | 7/2004 | Wood |
| 2006/0085027 A1 * | 4/2006 | Santin et al. .................. 606/199 |
| 2006/0207598 A1 | 9/2006 | Thomas |
| 2006/0259065 A1 | 11/2006 | Maryanka |
| 2007/0191876 A1 | 8/2007 | Dubrul et al. |
| 2008/0009897 A1 | 1/2008 | Duran Von Arx |
| 2008/0167676 A1 | 7/2008 | Howard |
| 2009/0093840 A1 | 4/2009 | MacDonald |
| 2009/0198268 A1 | 8/2009 | Case |
| 2009/0248058 A1 | 10/2009 | Kotler |
| 2009/0272386 A1 | 11/2009 | Kurtz |
| 2010/0063532 A1 | 3/2010 | Moore |
| 2010/0100181 A1 * | 4/2010 | Makower et al. ............... 623/10 |
| 2010/0106255 A1 | 4/2010 | Dubin |
| 2010/0211181 A1 | 8/2010 | Prabhu et al. |
| 2010/0319708 A1 | 12/2010 | Mahr et al. |
| 2011/0034950 A1 | 2/2011 | Toriumi |
| 2011/0118775 A1 | 5/2011 | Brown |
| 2011/0226264 A1 * | 9/2011 | Friedman et al. ............. 128/848 |
| 2011/0270297 A1 | 11/2011 | Judd |
| 2012/0046756 A1 | 2/2012 | Want et al. |
| 2012/0130476 A1 * | 5/2012 | Paul et al. .................... 623/1.13 |
| 2013/0090720 A1 | 4/2013 | Marh et al. |
| 2013/0231753 A1 * | 9/2013 | Liddy et al. .................. 623/23.7 |
| 2013/0261763 A1 * | 10/2013 | Shalon et al. ................. 623/23.7 |
| 2013/0296809 A1 * | 11/2013 | Santin et al. .................. 604/285 |
| 2014/0018839 A1 * | 1/2014 | Renner et al. ................. 606/199 |
| 2014/0150804 A1 * | 6/2014 | Shalon ......................... 128/848 |

* cited by examiner

NASAL STENT

This application takes the benefit of United Stated Provisional Application 61/811,721 filed on Apr. 13, 2013 under 35 U.S.C §119(e).

BACKGROUND OF THE DISCLOSURE

Field of the Disclosure

The disclosure relates to nasal valve stent devices and more particularly pertains to a new nasal valve stent device for improving airflow through the nasal cavity of a person's nose.

SUMMARY OF THE DISCLOSURE

An embodiment of the disclosure meets the needs presented above by generally comprising an assembly configured for positioning within a person's nasal cavity to enlarge the nasal cavity and promote easier breathing through the person's nose. The assembly comprises a frame having a pair of ends and a plurality of rib elements extending between and being attached to each of the ends. The rib elements are arched between the ends to form a cage like structure having a hollow interior. The rib elements are spaced from each other such that air freely flows through the frame. The frame is configured for being positioned within an inner nasal valve of the nose.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
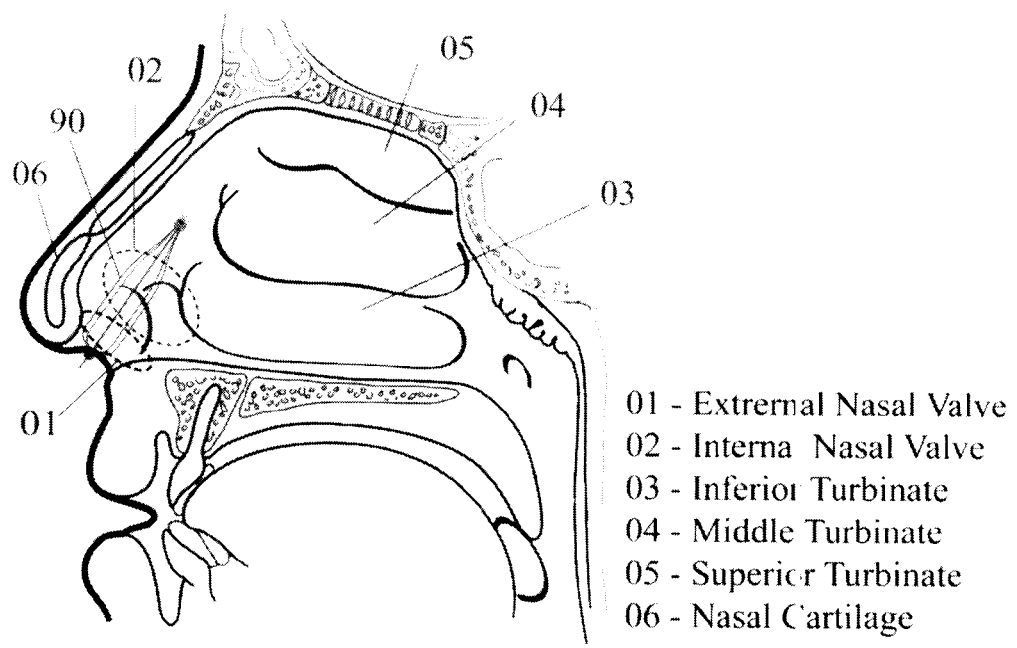
FIG. 1 is an in-use view of a nasal valve retention stent assembly according to an embodiment of the disclosure.

With reference now to the drawings, and in particular to FIGS. 1 through 18 thereof, a new nasal valve stent device embodying the principles and concepts of an embodiment of the disclosure and generally designated by the reference numeral 10 will be described.

In the following description, numerous specific details are set forth in order to provide a thorough understanding of the present invention apparatus, method of use and fabrication processes. It will be apparent, however, to one skilled in the art, that the present method and apparatus may be practiced without these specific details. Reference in the specification to "one embodiment" or "an embodiment" means that a particular feature, structure, or characteristic described in connection with the embodiment is included in at least one embodiment. The appearances of the phrase "in one embodiment" in various places in the specification do not necessarily all refer to the same embodiment. Thus, while assembly 10 does represent one general embodiment, other general embodiments are found at 60, 70 and 90, for example, as well.

As best illustrated in FIGS. 1 through 18, the nasal valve retention stent assembly 10 generally comprises an assembly capable of maintaining a nasal valve 02 in an open condition and, therefore, allowing for an improvement of patient breathing. The nasal valve retention stent assembly 10 of the invention includes a frame 11. It should be understood that a pair of assemblies 10 may be used together and may further be connected by a flexible coupling element 13. The construction of the assembly 10 enables the expansion of separate internal nasal valves 02 independently. This may be significant where the nasal cavities of a user's nose are asymmetrical. The flexible coupling element 13 connects both a pair of frames 11 together and simultaneously acts as a safety mechanism to prevent accidental displacement in the nasal cavity. After insertion, the coupling element 13 holds both frames 11 in place, thereby maintaining the proper expansion of the internal nasal cavities. Distal ends 12 of the frames 11, with respect to the coupling element 13, may have silicone buffers positioned thereon that protect the internal nasal valve 02 tissue against accidental scratching. A series of rib elements 14 in the form of arched elongated members create a cage like structure. By "cage like" what is meant is that the internal area of the frame 11 is substantially hollow when in an expanded configuration such that the rib elements 14 are spaced from each other, thus allowing air to freely flow through the frame 11. By arching the rib elements 14, the frame 11 is biased outwardly from a longitudinal axis extending through its ends, which enables the device to apply constant gentle pressure by each rib independently and forming into any internal size of a nasal valve. For increased comfort, the frame 11 may be coated with a protective silicon material, which would be medical grade silicon, or an elastomeric material.

Different configurations of the nasal valve retention stents will be discussed throughout this Specification and shown in the Figures. The various configurations demonstrate a number of possible arrangements of the frame 11 while maintaining the underlying structure and function of the assembly including its use as a nasal valve retention stent and its method of usage. While various configurations will be addressed, it should be understood that the method of constructing each configuration may be accomplished in one of a plurality of manners as discussed below.

Figure 2:
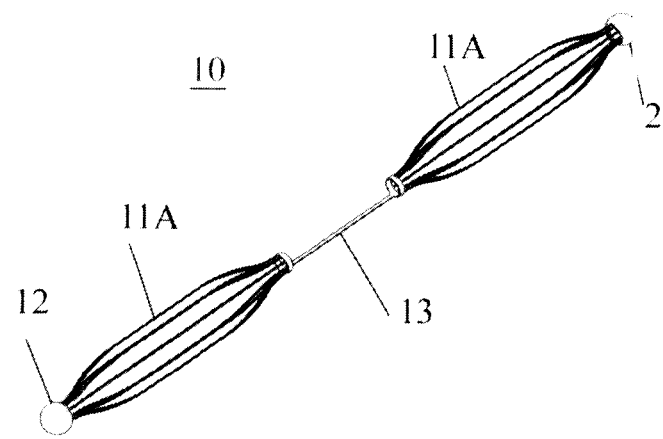
FIG. 2 is a front perspective view of an embodiment of the disclosure.
Figure 3:
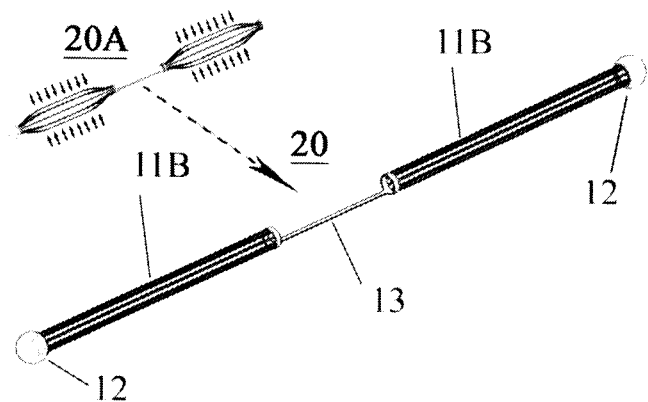
FIG. 3 is a front perspective view of an embodiment of the disclosure.

Generally, the assembly 10, and more particularly the frame 11, may be comprised of a material having temperature deformable characteristics. First instance, the frame 11 may have an expanded condition 11A, having a cage like structure, as shown in FIG. 2 when a first temperature condition is met or the frame 11 may have a compressed condition 11B as shown in FIG. 3 when a second temperature condition is met. It should be clear from the Figures that the terms "expanded" and "compressed" are related to a diameter of the frame 11 taken perpendicular to a longitudinal axis of the frame 11. The frame 11 may be positioned in relatively cool water, for instance, to cause the frame 11 to deform into the compressed condition 11B such that it may easily be extended through the external nasal valve 01 and into the internal nasal valve 02. Once within the internal nasal valve 02, the user's body heat will raise the temperature of the frame 11A causing it to deform into the expanded condition 11B. The shaft altering ability of the frame 11 may be accomplished in by utilizing any commonly known shape memory alloys. For example, one type of shape memory alloy which may be used is available under the trade name Nitinol. The Nitinol utilized may be an alloy having a Nickel composition ranging from 54.5% to 55.0%. With respect to the frame 11, the material would allow deformation, such as by hand, to the compressed condition at temperatures of less than about, for example, 20° C. and which will "remember" its shape and return to its expanded condition above 30° C. such that it will retain the expanded condition when subjected to the body heat of the user. This temperature is of course related to the type of material being used and typically the temperature allowing deformation by hand to the compressed condition would be greater than 0° C. and less than 20° C.

However, it should be understood that the assembly 10 may be comprised of materials that are not shape memory materials which do not deform when subjected to minor changes in temperatures. Thus, the assembly 10 may be comprised of metals such as surgical stainless steel or may be comprised of a polymer material. For instance, 316LVM stainless steel may be utilized. Moreover, the assembly 10 may be comprised of a resiliently bendable material. Alternatively, super elastic Nitinol having a nickel content of 55.8% to 60.0%. Super elastic materials are those having deformation capabilities at temperatures far below their in use temperature. In this case, a super elastic Nitinol may have deformation temperature of less than −10° C. For reasons stated below, there may be particular advantages for using a material that is deformable at a temperatures near to the in-use temperature.

The frame 11, in the expanded condition, will have a generally cylindrical, obround or elliptical shaped body constructed from arced, wire-like rib elements 14 which form the body. More particularly, the ends of the body may be cone shaped. The rib elements 14 may comprise either a solid wire construction or a tubular construction. A maximum diameter of the body may generally be between 6.0 mm and 9.0 mm and the frame will typically have a length between 40.0 mm and 54.0 mm.

FIG. 1 illustrates a coronal section of the nasal cavity which shows the description of the nasal cavity organs referenced herein. FIG. 1 also shows an example of nasal valve retention stent assembly 90. As seen in FIG. 1, the assembly 90 expands the orifice of the nostril, the internal nasal valve 02 and the external nasal valve 01. As previously stated, assembly 90 is one of many configurations as indicated by reference characters 10, 20, 60, 80, 90 and 150.

FIG. 2 illustrates an example of the assembly 10 having two self-expanding frames 11A that are connected by the flexible coupling element 13. Self-expanding nasal stents herein are comprised of a shape memory material such as Nitinol tubing and thereafter shape-set to retain its expanded configuration at an elevated temperature. The flexible coupling 13 connects a pair of self-expanding frames 11A having buffers, which may be comprised of a silicone material, permanently attached on their distal ends 12 used as a protection against accidental scratching of the internal valve tissue. A process of making and assembling assembly 10 is described in more detail in FIGS. 4, 5, 6 and 7. Alternatively, the frames 11A may be comprised of a material which is permanently set to a particular shape and thus may be comprised of one of the alternative materials discussed above. Such materials would retain the frames 11A in their expanded condition.

FIG. 3 depicts an embodiment of the nasal stent assembly 20 having two self-expanding frames that are connected by the flexible coupling element 13. Assembly 20 is shown in its deformed, or compressed condition. FIG. 3 further shows the assembly 20 as 20A in an expanded condition wherein the frame 11B is compressed for insertion into the nasal cavities. The compression process may be simply performed, for example, by placing the frame 11B under running cold water and by applying radial pressure on the frame 11B. At room temperature, the device may be easily deformed and will remain compressed until insertion. This is possible due to the unique properties of shape memory material which will cause the frame 11B to move back to its expanded condition at body temperature. Room temperature is generally defined as between about 26° C. and 16° C.

Figure 4:
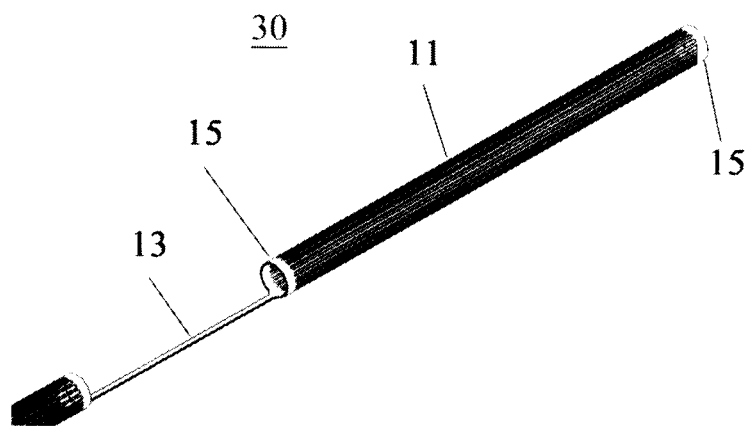
FIG. 4 is a broken perspective view of an embodiment of the disclosure.

A method that may be used to construct the nasal valve retention stent apparatus 30 is illustrated in FIG. 4. In the embodiment shown in FIG. 4, the body shape of the stent apparatus 30 originally comprised shape memory tubing, or a super elastic material, having longitudinal slits cut therein. The diameter of the tubing is between 1 to 2.5 mm and 100 to 135 mm in total length for the typical assembly (10 or 20) components including two frames 11 and the coupling 13. The process of laser cutting slits creates rib elements 14. Distal and proximal rings 15, with respect to the coupling 13, create junctions for the rib elements 14. The flexible coupling 13 may be created by cutting out a portion of the tubing material by the laser. The flexible coupling 13 connects the frames 11 together.

Figure 5:
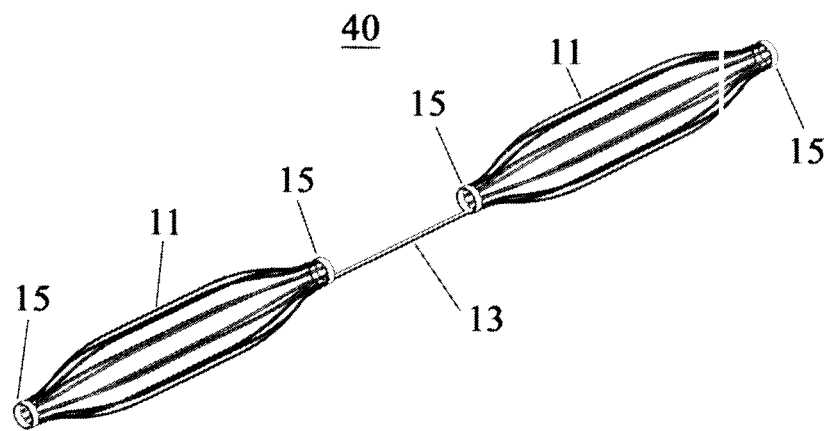
FIG. 5 is a front perspective view of an embodiment of the disclosure.

FIG. 5 illustrates assembly 40 comprising two frames 11 each including of two junction rings 15 and the connecting flexible coupling 13. The assembly 40 is a representation of both assemblies 10 and 20, which may be constructed of shape memory or super-elastic Nitinol alloy tubing. After laser cutting, the assembly 40 is exposed to electro polishing following a "shape setting" process as is known in the art of shaping shape memory alloys.

Figure 6:
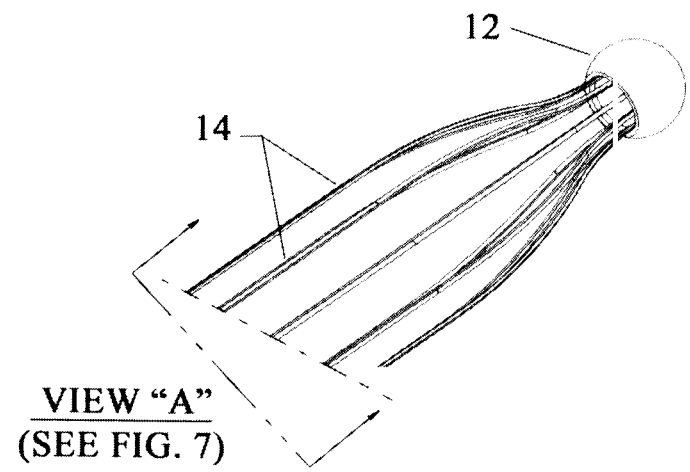
FIG. 6 is a broken perspective view of an embodiment of the disclosure.

FIG. 6 depicts a buffer 12 which are positioned on the distal end 15 of assembly 10, for example, though such a buffer may be placed on multiple ones of the embodiments discussed herein. The buffers may comprise a silicone material though other materials including plastics, elastomers and the like may be utilized to prevent irritation of the nasal cavity. Alternatively, the distal end 15 may be a rounded, bulbous member of metal or other material. The buffer 12 is permanently attached to the distal end 15 of each frame 11. The diameter of the buffer 12 will typically be 3.0 mm or less.

Figure 7:
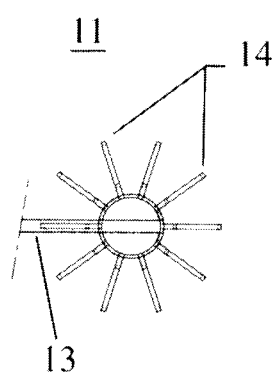
FIG. 7 is a cross-sectional view of an embodiment of the disclosure taken along line 7-7 of FIG. 6.

FIG. 7 depicts the cage like structure which is formed when the assembly 10 or 20, for example is in the expanded condition. The rib elements 14 generate a constant gentle pressure on the nasal valve tissue. After insertion, the rib elements 14 retain the nasal valve tissue expanded and allow improved breathing.

Figure 8:
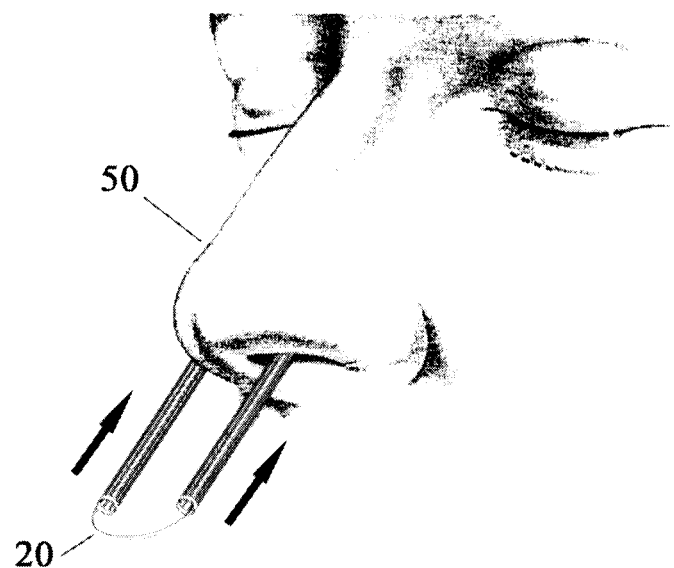
FIG. 8 is a perspective in-use view of an embodiment of an injector of the disclosure.

The assembly 20, as shown in FIG. 8, may be used for expansion of a patient's internal nasal cavity. Assembly 20 is inserted into a patient's nose 50 directly in its deformed, compressed condition without using an injector 100, as will be described further below. The assembly 20, if made of a shape memory material may be deformed at room temperature, as described previously and then inserted into the nasal cavity. As the body temperature warms up the material, the shape of both frames 11 will transform to their "memorized" expanded condition, gently pressurizing the nasal valve cavities by each rib element 14 maintaining the proper expansion of the internal nasal valve cavities.

Figure 9A:
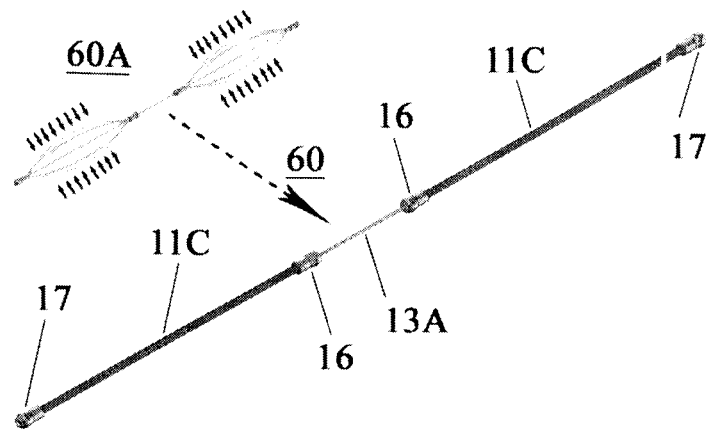
FIG. 9A is a front perspective view of an embodiment of the disclosure.
Figure 9B:
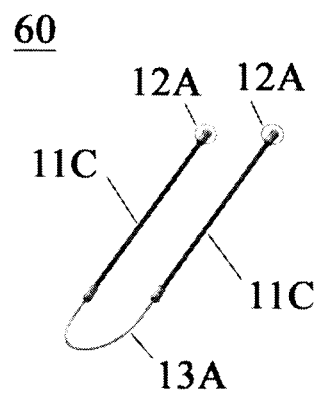
FIG. 9B is a front perspective view of an embodiment of the disclosure including an injector.
Figure 9C:
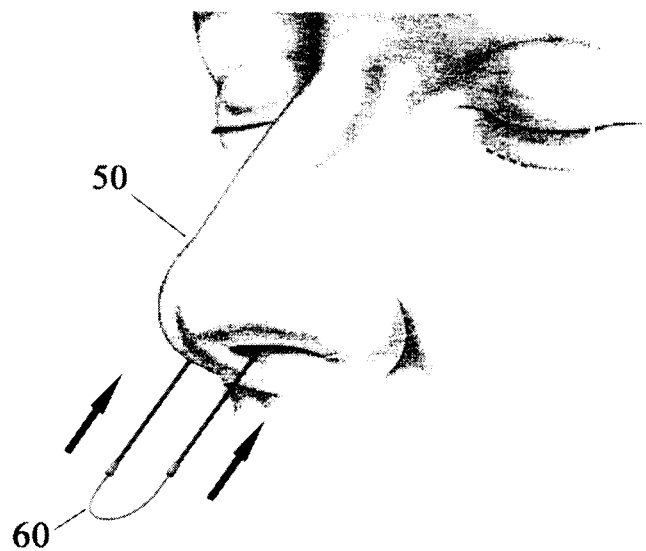
FIG. 9C is a perspective in-use view of an embodiment of the disclosure shown in FIG. 9B.

FIG. 9A illustrates another example of the nasal stent sub-assembly 60 having two self-expanding frames 11C that are connected by the flexible coupling element 13A. The frames 11C and coupling 13A may each be comprised of shape memory material. However, the coupling 13A may be joined to the frames 11C with joints 16 that may comprise titanium or stainless steel such as hypodermic or other miniature tubing material machined from rod. The joints are then compressed over wires of frame 11C. FIG. 9B includes spherical silicone buffers 12A, permanently attached to each distal end 17 of each frame, that provide protection of the proximal ends of both frames 11C. The diameter of the cylindrical silicone buffer 12A is typically 3.0 mm or less whichever may be suitable for use with the proposed system. As shown in FIG. 9C, the insertion process is similar as described in FIG. 8.

Figure 10A:
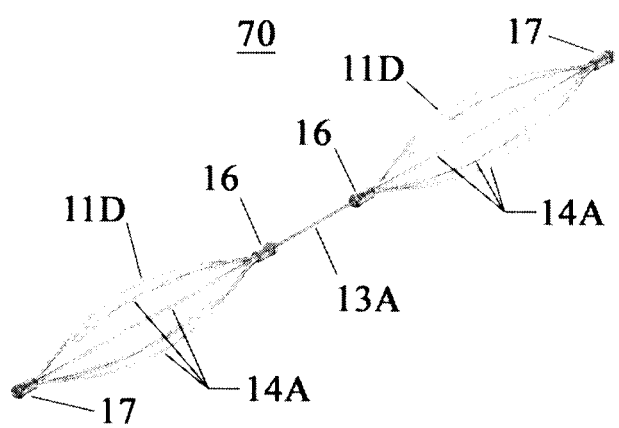
FIG. 10A is a front perspective view of an embodiment of the disclosure.

FIG. 10A depicts the embodiment of assembly 70 comprising a resilient wire material or polymer material. The assembly 70 has two permanently expanded frames that are connected by a flexible coupling element 13A. The frames 11D are made of a super elastic Nitinol or a stainless steel wire and thereafter shape-set to retain its expanded configuration. The frames 11D may be made of a polymeric material by injection molding and composed into assembly 70 by connecting both frames 11D either by wire or polymeric coupling 13A. The joint 16 and 17 may be made of titanium or stainless steel such as hypodermic or other miniature tubing material or machined from rod. The joints 16 and 17 are then compressed over the frame wires 11D.

Figure 10B:
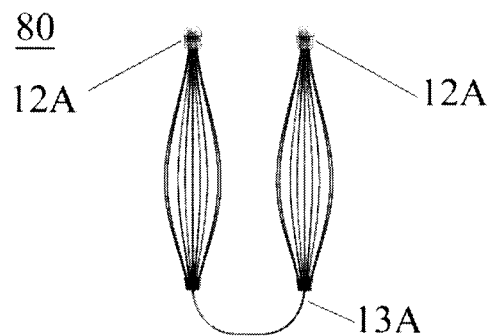
FIG. 10B is a top view of an embodiment of the disclosure.
Figure 10C:
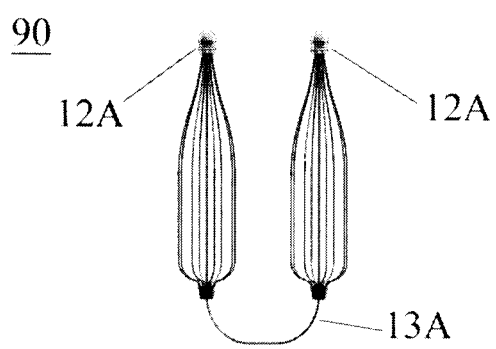
FIG. 10C is a top view of an embodiment of the disclosure.
Figure 10D:
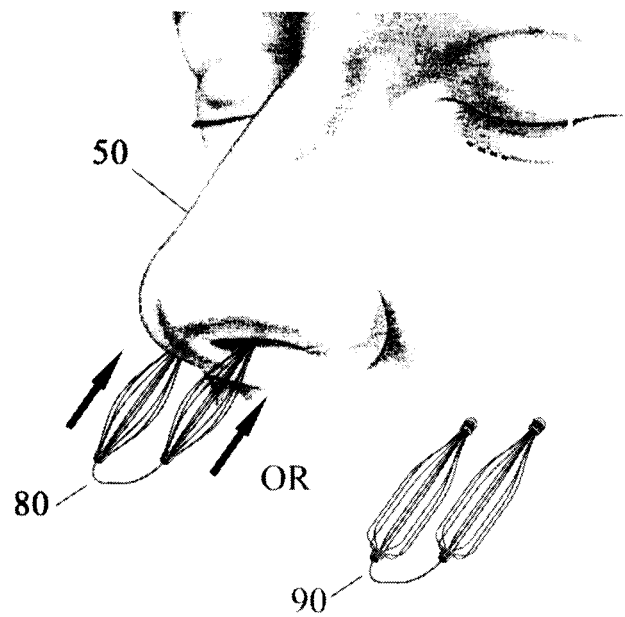
FIG. 10D is a front perspective view of an embodiment of the disclosure and method of usage.

In examples shown in FIGS. 10B and 10C, the assembly 80, 90 can assume different shapes. Assembly 80 depicts a "bulb-like" useful for the expansion of both internal 02 and external 01 nasal valves whereas a "bottle-like" shape provided in assembly 90 is suitable for expansion of both nasal valves 01, 02 as well as the collapsed nostrils. FIG. 10D shows assembly 80 or 90 which may be inserted into a patient's nose 50 directly and remaining in its permanently expanded state without using an injector. After insertion, the apparatus frames gently pressurize the nasal valve cavities independently of each other by each expanded rib 14A (as shown in FIG. 10A), and, being resiliently bendable, will form into any internal size and shape of a nasal valve to maintain the proper expansion of the internal nasal valve cavities.

Figure 11:
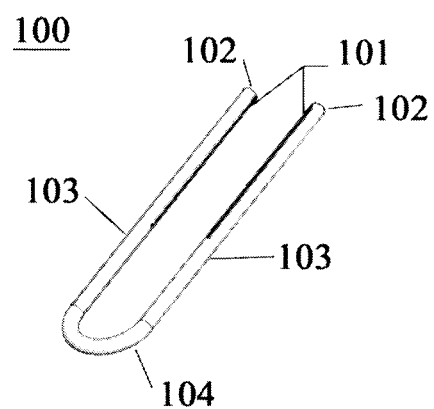
FIG. 11 is a front perspective view of an embodiment of an injector of the disclosure.
Figure 12:
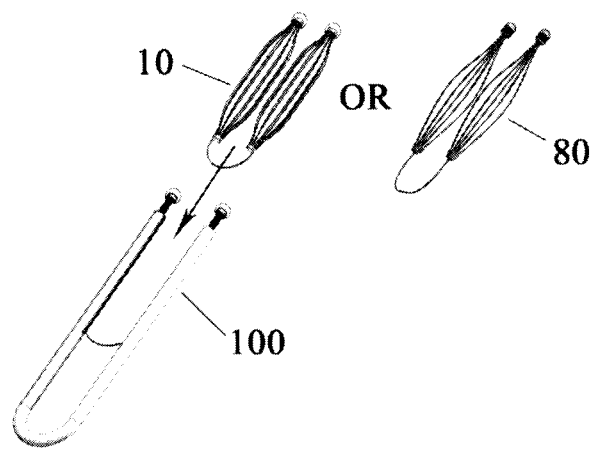
FIG. 12 is a front perspective view of an embodiment of a stent and injector of the disclosure.

FIG. 11 includes a nasal injector 100 configured to facilitate the insertion of the self-expanding nasal stent assembly 10 or 80 (as shown in FIG. 12) through the nostrils into the internal nasal valves. The nasal injector 100 may be made of a flexible silicone tubing 103 or any other elastomeric material, which allows for easy deformation represented by item 104 in its deformed bent state. The tubing 103 includes a pair of terminal ends 102 which are open. Slits 101 extend into the terminal ends and the slits are long enough to facilitate insertion of the assembly 10, 80 into the injector 100. FIG. 12 depicts the assembly 10 or 80, when compressed, and positioned in the injector 100.

Figure 13:
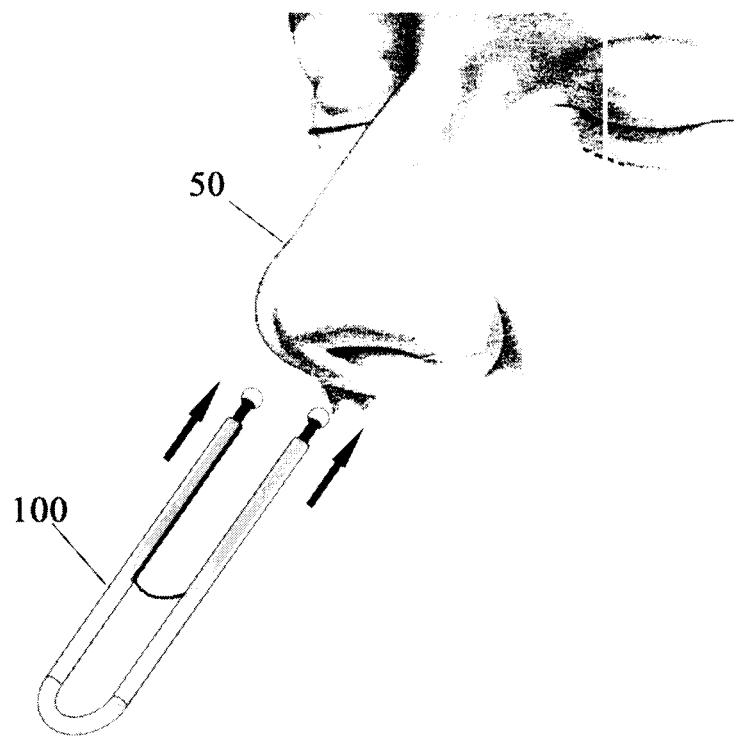
FIG. 13 is a front perspective view of an embodiment of a stent and injector of the disclosure.
Figure 14:
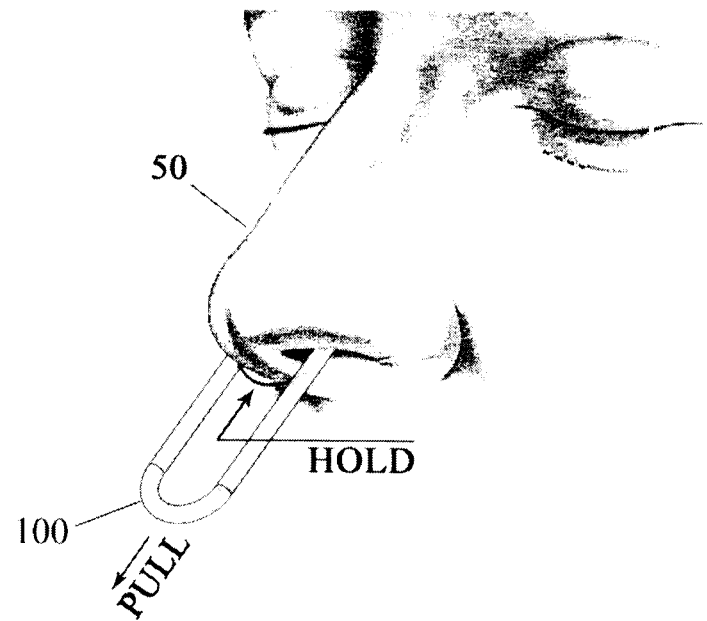
FIG. 14 is an in-use front perspective view of an embodiment of the disclosure.

As shown by the use of FIG. 13, the insertion process is similar as described in FIG. 8, 9C or 10D. The self-expanding nasal stent apparatus, in its deformed compressed stage, is laden inside the injector tubing 100 and ready for insertion. Hence, the patient may easily insert the injector 100 into their nasal cavities 50. After insertion of the injector 100 into the nasal cavities 50, as shown in FIG. 14 and by holding the coupling element 13 of the assembly 10, 80 (see HOLD), the injector 100 can then be pulled back (see PULL) leaving the assembly 10, 80 inside the nasal cavities. By pulling back the injector 100, the assembly 10,80 will warm and assume its relaxed, expanded condition similar as shown in FIG. 7, to generate constant pressure on the nasal valve tissue. After the insertion, the expanded frame 11 keeps both nasal valves open, thus allowing for improved breathing.

Figure 15:
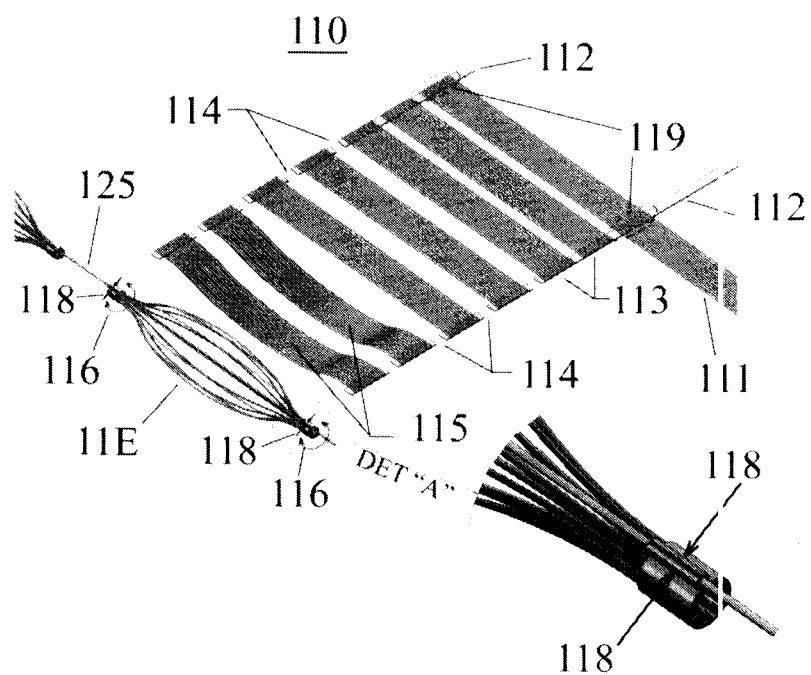
FIG. 15 is a rear perspective view of an embodiment of the disclosure depicting a step in a method of making the assembly.

FIG. 15 illustrates an automated fabrication process 110 of making the nasal stents apparatus from multiple wires 111 of a resilient material. The wires, which may be provided by a reel, are equally spaced and then permanently joined 119 with metallic ribbons 112 by a resistant or laser welding method. At a point 113 adjacent to the ribbon, the wires 111 are cut and the wires are welded to the ribbons 112 after which the ribbons 112 are separated at points 114 to form unfolded frame 11E. The cutting of the wires 111 may also be accomplished by a second step of the welding process by applying higher level energy pulses which melt the wires 111 instead of cutting them. The next step is pre-forming segments as shown at 115. The shape of the frame 11E is then formed as shown at 116 and the ribbons are welded onto a carrier wire 125 in the direction as indicated by item 118 shown in detail "A". This method allows for a fully automated process. In later steps, the ends of the frames 11E may be separated and protected by buffers 12 as previously described in FIGS. 3, 6, 9B, 10B and 10C.

Figure 16:
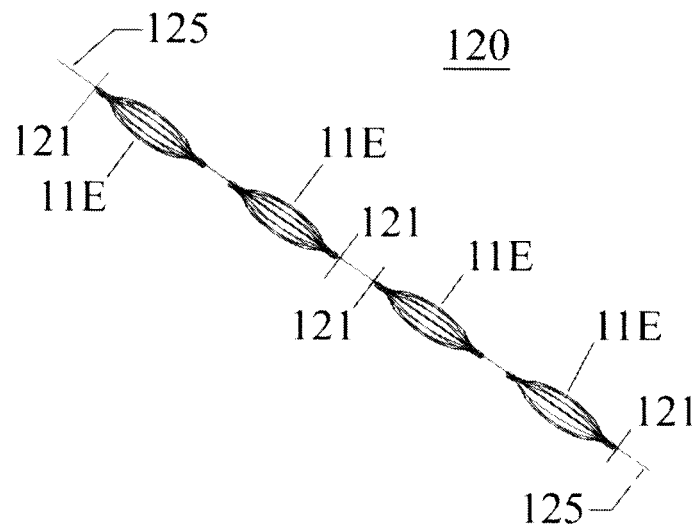
FIG. 16 is a rear perspective view of an embodiment of the disclosure depicting a step in a method of making the assembly

FIG. 16 provides a processed product 120 of the fabrication process described in FIG. 15 above. A chain of frames 11E may be separated in pairs by cutting the carrier wire 125 in places shown at 121. This step in the fabrication process creates a separated final frame assembly 130 or 140 shown in FIGS. 17A and 17B.

Figure 17A:
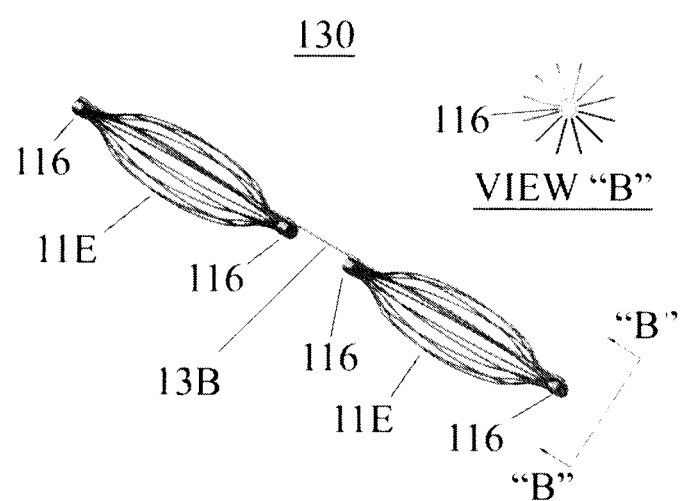
FIG. 17A is a rear perspective view of an embodiment of the disclosure.

FIG. 17A illustrates an assembly 130 embodiment connected by a coupling wire 13B and the ends 116 made from thin ribbons. Together, permanently attached wires and ribbons form the frame 11E. The frame wire-ribbons, or rib elements 14 formed by the frame wire-ribbons, create joints where the frame wires and the coupling wire stay connected in-side the ribbon joint. View "B" illustrates a view of the assembly 130 that has permanently expanded wires, creating a rib-like frame structure, that are welded internally with joint 116.

Figure 17B:
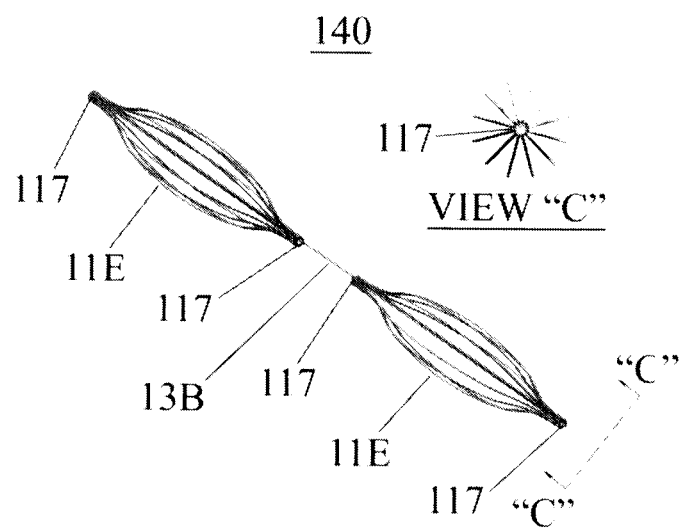
FIG. 17B is a rear perspective view of an embodiment of the disclosure.

FIG. 17B includes an assembly 140 embodiment whereby frames 11E are connected by a coupling wire 13B have joints 117 made of metallic ribbons permanently attached to rib elements. In this embodiment, both joints may have a wire forming frame and a coupling wire welded externally to the joint body. View "C" illustrates a view of the stent frame having permanently expanded rib elements, creating a rib-like frame structure, that are welded externally to the joint 117.

Figure 18:
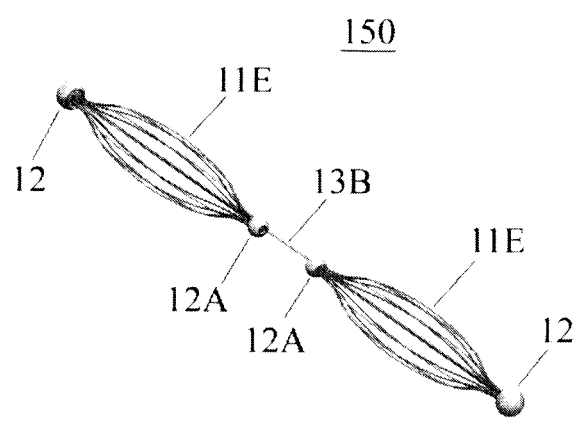
FIG. 18 is a rear perspective view of an embodiment of the disclosure.

FIG. 18 includes a complete nasal valve retention stent assembly 150 having silicone protection, or a buffer, permanently attached to the proximal and distal ends, 12A and 12 respectively, on both frames 11E. Frames 11E are connected by a flexible wire coupling 13B.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A nasal valve stent assembly configured for positioning within a person's nasal cavity to enlarge the nasal cavity and promote easier breathing through the person's nose, said assembly comprising:
   a frame having a pair of ends and a plurality of rib elements extending between and being attached to each of said ends, said rib elements being arched between said ends to form a cage like structure having a hollow interior and said rib elements being spaced from each other such that air freely flows through said frame; and
   a buffer being permanently attached to one of said ends;
   wherein said frame is configured for being positioned within an inner nasal valve of the nose.

2. The nasal valve stent assembly according to claim 1, wherein said rib elements are comprised of a shape memory material, said rib elements being retained in said cage like structure to define an expanded condition when a first temperature condition is met, said rib elements being deformable into a collapsed condition when a second temperature condition is met, wherein said first temperature condition is higher than said second temperature condition.

3. The nasal valve stent assembly according to claim 2, wherein said collapsed condition comprises said rib elements being substantially linear between said ends such that said frame has a tubular configuration.

4. The nasal valve stent assembly according to claim 1, wherein said cage like structure has a generally elliptical shape tapering to cones at said ends.

5. The nasal valve stent assembly according to claim 1, wherein said cage like structure has a generally tear-drop shape.

6. The nasal valve stent assembly according to claim 1, wherein said assembly includes a pair of said frames, a coupler being attached to and extending between said frames.

7. The nasal valve stent assembly according to claim 6, wherein each of said ends of said frames includes a distal end and a proximal end with respect to said coupler, said coupler being attached to said proximal ends.

8. The nasal valve stent assembly according to claim 7, further including a nasal injector configured to facilitate insertion of said frames through a person's nostrils, said nasal injector comprising tubing having a pair of terminal ends, said terminal ends being open, each of said terminal ends having a slit therein for receiving said coupler, wherein each of said frames is extendable into one of said terminal ends and said injector is thereafter configured to be extended through the person's nostrils to deposit said frames within the person's nostrils.

9. The nasal valve stent assembly according to claim 1, wherein said rib elements are comprised of stainless steel.

10. The nasal valve stent assembly according to claim 1, wherein said buffer is comprised of a silicone material.

11. The nasal valve stent assembly according to claim 7, further including a pair of said buffers, each of said proximal ends having one of said buffers permanently attached thereto.

12. The nasal valve stent assembly according to claim 11, wherein said buffers are each comprised a silicone material.

13. The nasal valve stent assembly according to claim 1, a protective coating being positioned on said frame.

14. The nasal valve stent assembly according to claim 12, wherein said protective coating comprises an elastomeric material or a silicon material.

15. The nasal valve stent assembly according to claim 6, a protective coating being positioned on each of said frames.

16. The nasal valve stent assembly according to claim 15, wherein said protective coating comprises an elastomeric material or a silicon material.

* * * * *